(12) United States Patent
Shi et al.

(10) Patent No.: US 8,212,003 B2
(45) Date of Patent: Jul. 3, 2012

(54) BIFUNCTIONAL FUSION PROTEIN WITH THROMBOLYTIC AND ANTICOAGULANT ACTIVITIES AND USES THEREOF

(75) Inventors: Bingxing Shi, Beijing (CN); Zuze Wu, Beijing (CN); Aiping Yu, Beijing (CN); Chunna Dong, Beijing (CN)

(73) Assignee: Institute of Radiation Medicine, Academy of Military Medical Sciences, PLA, Beijing (CN)

( * ) Notice: Subject to any disclaimer, the term of this patent is extended or adjusted under 35 U.S.C. 154(b) by 1014 days.

(21) Appl. No.: 10/526,682

(22) PCT Filed: Sep. 3, 2003

(86) PCT No.: PCT/CN03/00744
§ 371 (c)(1),
(2), (4) Date: Nov. 10, 2005

(87) PCT Pub. No.: WO2004/022598
PCT Pub. Date: Mar. 18, 2004

(65) Prior Publication Data
US 2006/0127389 A1    Jun. 15, 2006

(30) Foreign Application Priority Data

Sep. 3, 2002 (CN) .................................. 02 1 29086

(51) Int. Cl.
*A61K 38/48* (2006.01)
*C07K 14/00* (2006.01)

(52) U.S. Cl. ....... 530/350; 530/384; 514/12; 424/94.64; 424/9.1; 435/69.7

(58) Field of Classification Search .................. 530/384, 530/350; 514/12; 424/9.1, 94.64; 435/69.7
See application file for complete search history.

(56) References Cited

U.S. PATENT DOCUMENTS

| | | | | |
|---|---|---|---|---|
| 5,298,599 A | * | 3/1994 | Rezaie et al. | 530/350 |
| 5,434,073 A | * | 7/1995 | Dawson et al. | 435/216 |
| 5,759,542 A | | 6/1998 | Gurewich | |
| 6,015,787 A | * | 1/2000 | Potter et al. | 514/12 |
| 6,423,680 B1 | * | 7/2002 | Rigat et al. | 514/20.6 |

OTHER PUBLICATIONS van Zyl et al., Thrombosis Research 88, 419-426 (1997).*
Office Action issued Jan. 5, 2010 in connection with Japanese Patent Application No. 2004-533177, filed Sep. 3, 2003.
English translation of Office Action issued Jan. 5, 2010 in connection with Japanese Patent Application No. 2004-533177, filed Sep. 3, 2003.
Office Action issued Dec. 19, 2005 in connection with European Patent Application No. 03 793 572.3, filed Sep. 3, 2003.
Office Action issued Jul. 14, 2009 in connection with Japanese Patent Application No. 2004-533177, filed Sep. 3, 2003.
English translation of Office Action issued Jul. 14, 2009 in connection with Japanese Patent Application No. 2004-533177, filed Sep. 3, 2003.
Van Zyl, Wlada B., et al., "Production of a Recombinant Antithrombotic and Fibrinolytic Protein, Platsak, in *Escherichia coli*," Thrombosis Research, 1997, 88:419-426.
Szarka, S.J., et al., "Staphylokinase as a Plasminogen Activator Component in Recombinant Fusion Proteins," Applied and Environmental Microbiology, Feb. 1999, 65:2 p. 506-513.
Wirsching, Frank, et al., "Modular Design of a Novel Chimeric Protein with Combined Thrombin Inhibitory Activity and Plasminogen-Activating Potential," Molecular Genetics and Metabolism, 2002, 75 p. 250-259.

* cited by examiner

*Primary Examiner* — Chih-Min Kam
(74) *Attorney, Agent, or Firm* — Cooper & Dunham, LLP

(57) ABSTRACT

This application relates to a fusion protein, which is composed of a thrombolytic protein, an anticoagulant protein, and a linker peptide. In particular, the fusion protein is composed of an anticoagulant protein and a protein molecule having plasminogen-activating activity, wherein said two proteins are linked together via a linker peptide, which can be recognized and cleaved by blood coagulation factors. The application also relates to the medical use of said fusion protein, and to the use of the linker peptide which can be recognized by blood coagulation factor in linking a thrombolytic protein and an anticoagulation protein.

6 Claims, 2 Drawing Sheets

Figure 1  Illustration of the fusion protein.
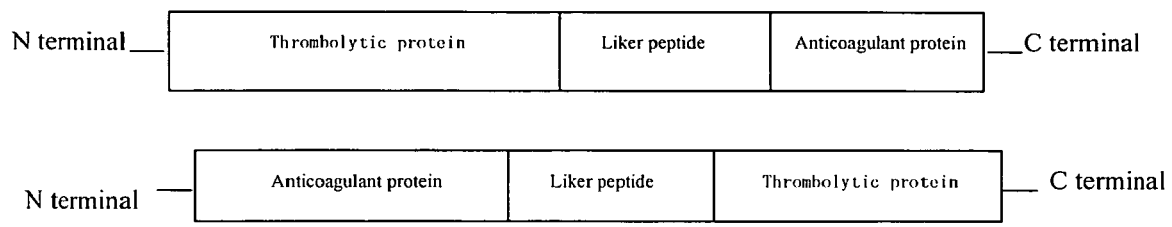

Figure 2  An electrophoresis map of genes of the fusion protein, staphylokinase and hirudin.
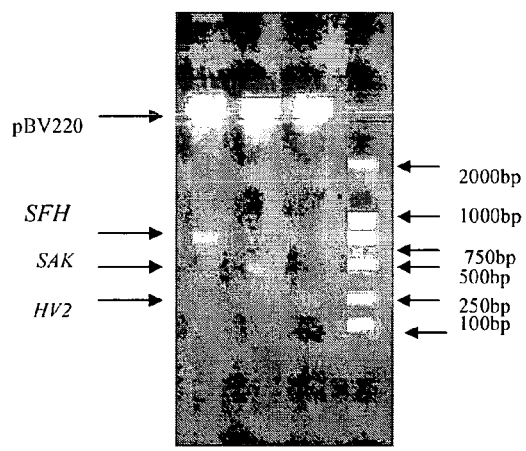

BIFUNCTIONAL FUSION PROTEIN WITH THROMBOLYTIC AND ANTICOAGULANT ACTIVITIES AND USES THEREOF This application is a 371 of PCT/CN03/00743, filed Sep. 3, 2003, which claims benefit of Chinese application CN 02129086.5, filed Sep. 3, 2002.

TECHNICAL FIELD

This application relates to a fusion protein, which is composed of a thrombolytic protein, an anticoagulant protein, and a linker peptide. In particular, the fusion protein is composed of an anticoagulant protein and a protein molecule having plasminogen-activating activity, wherein said two proteins are linked together via a linker peptide, which can be recognized and cleaved by blood coagulation factors. The application also relates to the medical use of said fusion protein, and to the use of the linker peptide which can be recognized by blood coagulation factor in linking a thrombolytic protein and an anticoagulation protein.

BACKGROUND OF INVENTION

Cardiovascular diseases are the leading causes of deaths of human being. Presently, urokinase and tissue-type plasminogen activator are used in clinic as major thrombolytic drugs, while heparin and hirudin are used as major anticoagulant drugs. Although thrombolytic therapy is successful in decreasing the death rate of patients suffering from thrombus, re-thrombus will often occur due to the entering of small gore into blood circulation. Therefore, heparin or hirudin is now used as anticoagulant agents in combination with thrombolytic agents for thrombolytic therapy.

However, thrombolytic agents and anticoagulant agents usually cause systematic haemolysis and anticoagulation due to their poor specificity, thereby leading to systematic haemorrhage.

In particular, tissue-type plasminogen activator (t-PA), streptokinase (SK), urokinase (UK) and urokinase-like plasminogen activator (u-PA) can activate the plasminogen, which in turn lyses clots at the site of thrombus. However, the activated plasminogen will also cause bleeding in non-thrombus locus. Staphylokinase (SAK) is a new plasminogen activator of native origin, and has certain specificity to the thrombus.

Hirudin (HV), which is a small protein, is regarded as the new anticoagulant agent due to its high affinity and selective inhibition to thrombin. However, hirudin is inclined to cause systematic haemorrhage in clinic. Moreover, there is no antagonist against hirudin hitherto.

Thus, to decrease side effects and increase therapeutic effects of thrombolytic drugs, it is important to increase their selectivity, targeting property and local concentration at thrombus clots, and to decrease drug concentration or activity at thrombus-free sites and the side effect of bleeding. The fusion protein in the prior art cannot reduce the side effect of bleeding.

Therefore, the development of anti-thrombus drug is focused on bifunctional medicament having both thrombolytic and anticoagulant activities. To combine thrombolytic activity with anticoagulant activity, the fusion of hirudin with SAK or SK have been studied. It showed that, if the N-terminal of hirudin was linked to C-terminal of SAK or SK, the hirudin will loss its anti-thrombin activity, while the plasminogen-activating activity of the thrombolytic protein is retained or partially retained; if the C-terminal of hirudin is linked to N-terminal of SAK, then due to the rapid degradation of N-terminal of SAK in vivo, the fusion protein will undergo degradation before functioning. Thus it is attracting in thrombolytic therapy to develop fusion protein having both thrombolytic and anticoagulant activities.

Purpose of Invention

The purpose of this invention is to provide a fusion protein having both thrombolytic and anticoagulant activities.

Disclosure of the Invention

This invention is based on the following recognition: a fusion protein can be constructed by linking a thrombolytic protein and an anticoagulant protein via a peptide containing blood coagulation factor-recognizable sequence. Thus constructed fusion protein provides several advantages as follows: Firstly, the fusion protein retains plasminogen-activating activity and thus the thrombolytic activity; Secondly, the N-terminal of the anticoagulant protein such as hirudin is linked to C-terminal of the thrombolytic protein, and thus the whole fusion protein doesn't show anticoagulant activity at thrombus-free sites and in vitro, thereby eliminating or reducing the side effect of bleeding caused by the anticoagulant protein such as hirudin; Thirdly, the fusion protein has the ability of targeting to clots due to the high affinity of hirudin to thrombin at thrombus locus, and thus it increases drug concentration at thrombus locus and decreases the therapeutical amount of the drug; Fourthly, when the fusion protein circulates to the locus of thrombus, the blood coagulation factor, which is involved in thrombosis and is characteristic of the thrombus, rapidly cleaves the fusion protein at the designed recognition site, and relieves the free thrombolytic protein and anticoagulant protein, thereby functioning both thrombolytic and thrombolytic activities. The invention has been established in terms of the above advantages.

In one aspect, the invention relates to a fusion protein composed of a thrombolytic protein, anticoagulant protein and a linker peptide.

In another aspect, the invention relates to a method for preparation of a fusion protein comprising a thrombolytic protein and an anticoagulant protein, which method comprises linking a thrombolytic protein gene and an anti-coagulant protein gene via a base sequence encoding IEGR (SEQ ID NO: 3) or LGPR (SEQ ID NO: 4) to form a gene encoding said fusion protein, and expressing said gene encoding the fusion protein in E. coli, yeast or animal cell lines to produce the fusion protein.

In a further aspect, the invention relates to a pharmaceutical composition comprising said fusion protein and a pharmaceutical acceptable carrier or excipient.

In a further aspect, the invention relates to the use of linker peptide containing a sequence recognized by blood coagulation factor in the preparation of a fusion protein comprising a thrombolytic protein and an anticoagulant protein.

In a further aspect, the invention relates to the use of a sequence which can be recognized and cleaved by blood coagulation factor as a linker peptide of a thrombolytic protein and an anticoagulant protein.

In still further aspect, the invention relates to a method for treatment of diseases or conditions associated with thrombosis, which method comprises administrating a therapeutically effective amount of the fusion protein to the patient suffering from thrombosis.

ILLUSTRATION OF THE DRAWINGS

The following drawings are presented to illustrate this invention, but they are not intended to limit the invention.

FIG. 1 is an illustration of the fusion protein.

FIG. 2 shows the electrophoresis of the fusion protein gene, staphylokinase (SAK) gene and hirudin (HV2) gene.

As used herein, the term "thrombolytic protein" refers to the proteins having thrombolytic activity, for example staphylokinase (SAK), tissue-type plasminogen activator (t-PA), streptokinase (SK), urokinase (UK), urokinase-like plasminogen activator (u-PA), venom and mutants thereof which activate other hemolytic factors or have thrombolytic activity per se. Staphylokinase (SAK) or mutant thereof is preferred.

As used herein, the term "anticoagulant protein" refers to the proteins having anticoagulant activity, such as hirudin, antithrombin III, venom and mutants thereof. Hirudin or mutant thereof is preferred.

1). The primer matched with downstream of the hirudin gene contains a Pst I restriction site. The hirudin gene with a FXa recognition sequence GSIEGR (SEQ ID NO: 5) is digested by two enzymes of BamH I and Pst I, and the above vector pBVSAK is also digested by BamH I and Pst I. The digested hirudin fragment is inserted into the digested vector pBVSAK to form plasmid pBVSFH (see FIG. 1). Said two gene fragments can also been linked by overlapping PCR method. The plasmid pBVSFH is transformed in *E. coli*, and induced to express at 42° C. The desired fusion protein (SFH) is obtained by ion exchange and gel filtration method in a purity of more than 96%. The SFH fusion protein comprises three domains, a SAK sequence, FXa recognition sequence GSIEGR (SEQ ID NO: 5) and hirudin. The amino acid sequence of SFH fusion protein is as follows:

```
  1 sssfdkgkyk kgddasyfep tgpylmvnvt gvdgkgnell sphyvefpik
 61 pgttltkeki eyyvewalda taykefrvve ldpsakievt yydknkkkee
101 sfpitekg  fvvpdlsehi knpgfnlitk viiekkgsie gritytdcte sgqdlclceg
161 snvcgkgnkc ilgsngeenq cvtgegtpkp qshndgdfee ipeeylq (SEQ ID NO: 2)
```

As used herein, the term "linker peptide recognized by blood coagulation factor" refers to the tetrapeptide of IEGR (IleGluGlyArg) (SEQ ID NO: 3), peptide containing IEGR sequence, tetrapeptide of LGPR (LeuGlyProArg) (SEQ ID NO: 4) or peptide containing LGPR sequence.

As used herein, the term "diseases or conditions associated with thrombosis" refers to any disease or condition caused by thrombus, such as cerebral thrombus, arterial thrombus, stroke and atherosclerosis.

As used herein, the term "patient" refers to mammals, particularly human being.

According to this invention, the fusion proteins is preferably a SFH fusion protein (SAK-GSIEGR-HV2) composed of staphylokinase and hirudin linked by GSIEGR (SEQ ID NO: 5), a fusion protein (tPA-PRIEGR-HV2) composed of tissue-type plasminogen activator (t-PA) and hirudin linked by PRIEGR (SEQ ID NO: 6), or a fusion protein (SAK-GSLGPR-HV2) composed of staphylokinase and hirudin linked by GSLGPR (SEQ ID NO: 7).

According to the invention, the fusion protein may be expressed in *E. coli, Pichia pastoris, Saccharomyces cerevisiae* or animal cells. Preferably, it is expressed in *E. coli* or yeast cells.

The following Examples are intended to illustrate the invention, but not mean to limit the invention.

EXAMPLES

Example 1

Preparation of Fusion Protein SFH (SAK-GSIEGR-HV2) and its Bifunctional Activities Eco R I and BamH I restriction sites are added to the two ends of SAK gene, respectively. The SAK gene without the stop codon is introduced in the vector pBV220, resulting in pBVSAK. By PCR method, the BamH I restriction site and the sequence coding FXa recognition sequence GSIEGR (SEQ ID NO: 5) are incorporated upstream of hirudin gene via a primer (5'-CG GGA TCC ATC GAA GGT CGT ATT ACT TAC ACT GAT TGT ACA GAA TCG-3'). (SEQ ID NO:

The thrombolytic activity of the purified fusion protein was determined using chromogenic substrate S-2251. To test thrombolytic and anticoagulant activity of the fusion protein in vivo, mouse-tail thrombosis MTT was induced by kappa-carrageenin. The results show that the anticoagulant activity of the SFH fusion protein is significantly higher than that of SAK. In particular, after induction by kappa-carrageenin for 24 hrs, SAK is i.p. injected at a dose of 1.2 mg/kg body weight every eight hours, and the inhibition of the tail thrombus is 36.6%. However, when equimolar SFH is administrated at a dose of 1.8 mg/kg body weight, the inhibition of the tail thrombus is 100%. After induction by kappa-carrageenin for 36 hrs, the inhibition of the tail thrombus reaches 18.2% and 90% respectively by SAK and SFH administrated as above. The detailed results are shown in Tables 1-3.

TABLE 1

Thrombolytic activity of fusion protein(SFH) and staphylokinase(SAK) determined by using chromogenic substrates (S-2251) (Reaction time is 5 min. n = 3, Δ OD$_{405}$)

| Samples | SAK | SFH |
| --- | --- | --- |
| Δ OD$_{405}$ | 0.357 ± 0.22 | 0.394 ± 0.01 |

Note:
2 nM fusion protein and 2 nM staphylokinase were used for determination.

TABLE 2

Anticoagulant activity of fusion protein(SFH) activated by FXa

| Samples | Anticoagulant activities |
| --- | --- |
| Fusion protein not cleaved by FXa | 0 |
| Fusion protein cleaved with 0.2 U of FXa for 10 min | 2560 ATU |

Note:
5.8 μg of the fusion protein SFH and 0.2 U of FXa were co-incubated for 10 min at 37° C. Clot method was used for determination of the anticoagulant activity.

TABLE 3

In vivo anti-thrombus activities of the fusion protein SFH and staphylokinase (SAK) (n = 10)

| kappa-carrageenin-inducing time (hr) | No. animals of each group | SAK | SFH |
|---|---|---|---|
| 24 | 10 | 36.6% | 100% |
| 36 | 10 | 18.2% | 90% |

Note:
SAK is i.p. administrated at a dose of 1.2 mg/kg body weight every eight hours, and equimolar SFH is administrated at a dose of 1.8 mg/kg. The animals used are Kunming mice (KM mice).

Table 1 shows that the fusion protein SFH exhibits the same level of thrombolytic activity as free staphylokinase. Table 2 shows that the intact fusion protein SFH does not exhibit anticoagulant activity, but shows entire anti-thrombus activity once cleaved by the blood coagulant factor FXa. Table 3 demonstrates that SFH has the significant anticoagulant effect. Thus the fusion protein of the invention indeed has both the thrombolytic and anticoagulant activities, and has lower side effect of hemorrhage.

Example 2

Preparation of Fusion Protein tPA-PRIEGR-HV2

Xho I and Avr II restriction sites are added to the upstream and downstream of tPA gene, respectively. The tPA gene without the stop codon is introduced in the vector pPIC9. The Avr II restriction site and the sequence coding FXa recognition sequence are incorporated upstream of hirudin gene via a primer using PCR method. The primer matched with downstream of the hirudin gene contains a Not I restriction site. The hirudin gene with a FXa recognition sequence is digested by two enzymes of Avr II and Not I, and the resulting fragment is linked into the above constructed vector pPIC9, wherein the introduced fragment is located downstream of tPA gene and forms the fusion gene TFH. Thus constructed plasmid is designed as pPIC9-TFH. The plasmids pPIC9-TFH and pPIC9K are digested by BamH I and Sal I. The TFH gene is then inserted into pPIC9K to form pPIC9K-TFH gene. The plasmid pPIC9K-TFH is linearized, and incorporated into yeast genome by electrotransformation. Methanol is used to induce the expression. The desired fusion protein TFH comprises three domains, a tPA sequence, FXa recognition sequence and hirudin.

Example 3

Preparation of Fusion Protein STH (SAK-GSLGPR-HV2) and its Bifunctional Activities EcoR I and BamH I restriction sites are added to the two ends of SAK gene, respectively. The SAK gene without the stop codon is introduced in the vector pBV220, resulting in pBVSAK. The BamH I restriction site and the sequence coding FXIIa recognition sequence GSLGPR (SEQ ID NO: 7) are incorporated upstream of hirudin gene via a primer using PCR method. The primer matched with downstream of the hirudin gene contains a Pst I restriction site. The hirudin gene with a FXIIa recognition sequence GSLGPR is digested by two enzymes of BamH I and Pst I, and the above vector pBVSAK is also digeste by BamH I and Pst I. The digested hirudin fragment is inserted into the digested vector pBVSAK to form plasmid pBVSTH. The sequence is confirmed by enzymatic digestion. Alternatively, said two gened fragments may be linked by overlapping PCR method. The plasmid pBVSTH is transformed into E. coli, and induced to express at 42° C. The desired fusion protein (STH) is obtained by ion exchange and gel filtration method in a purity of more than 96%. The STH fusion protein comprises three domains, a SAK sequence, FXIIa recognition sequence GSLGPR (SEQ ID NO: 7) and hirudin.

The invention claimed is:

1. A fusion protein comprising a thrombolytic protein, an anticoagulant protein, and a linker peptide recognized by blood coagulation factor, wherein said fusion protein is a fusion protein (SAK-GSIEGR-HV2) of staphylokinase and hirudin linked by linker peptide GSIEGR (SEQ ID NO: 5), a fusion protein (tPA-PRIEGR-HV2) of tissue-type plasminogen activator (t-PA) and hirudin linked by linker peptide PRIEGR (SEQ ID NO: 6), or a fusion protein (SAK-GSLGPR-HV2) of staphylokinase and hirudin linked by linker peptide GSLGPR (SEQ ID NO: 7).

2. A pharmaceutical composition comprising the fusion protein of claim 1 and a pharmaceutically acceptable carrier or excipient.

3. A method for the treatment of a disease or condition associated with thrombosis, comprising administrating a therapeutically effective amount of the fusion protein of claim 1 to a patient suffering from thrombosis.

4. A fusion protein, comprising a thrombolytic protein, an anticoagulant protein, and a linker peptide, wherein said fusion protein is a fusion protein (SAK-GSIEGR-HV2, or SFH) of staphylokinase and hirudin linked by linker peptide GSIEGR (SEQ ID NO: 5).

5. A pharmaceutical composition comprising the fusion protein of claim 4 and a pharmaceutically acceptable carrier or excipient.

6. A method for the treatment of a disease or condition associated with thrombosis, comprising administrating a therapeutically effective amount of the fusion protein of claim 4 to a patient suffering from thrombosis.

* * * * *

UNITED STATES PATENT AND TRADEMARK OFFICE
CERTIFICATE OF CORRECTION

PATENT NO. : 8,212,003 B2  
APPLICATION NO. : 10/526682  
DATED : July 3, 2012  
INVENTOR(S) : Shi et al.

It is certified that error appears in the above-identified patent and that said Letters Patent is hereby corrected as shown below:

On the title page Item [73] should read INSTITUTE OF RADIATION MEDICINE ACADEMY OF MILITARY SCIENCES, PLA, Beijing, China and BEIJING LU YIN LI HUA PHARMACEUTICAL SCIENCE & TECHNOLOGY DEVELOPMENT COMPANY, LTD, Beijing, China.

Signed and Sealed this
Twenty-second Day of April, 2014

Michelle K. Lee
*Deputy Director of the United States Patent and Trademark Office*

SEQUENCE LISTING

```
<160> NUMBER OF SEQ ID NOS: 7

<210> SEQ ID NO 1
<211> LENGTH: 47
<212> TYPE: DNA
<213> ORGANISM: artificial sequence
<220> FEATURE:
<223> OTHER INFORMATION: synthesized primer

<400> SEQUENCE: 1
cgggatccat cgaaggtcgt attacttaca ctgattgtac agaatcg        47

<210> SEQ ID NO 2
<211> LENGTH: 205
<212> TYPE: PRT
<213> ORGANISM: artificial sequence
<220> FEATURE:
<223> OTHER INFORMATION: SAK gene product and Hirudin gene product
      (from Hirudo medicinalis) linked by synthetic linker peptide
      sequence GSIEGR

<400> SEQUENCE: 2

Ser Ser Ser Phe Asp Lys Gly Lys Tyr Lys Lys Gly Asp Asp Ala Ser
1               5                   10                  15

Tyr Phe Glu Pro Thr Gly Pro Tyr Leu Met Val Asn Val Thr Gly Val
            20                  25                  30
```

-continued

```
Asp Gly Lys Gly Asn Glu Leu Leu Ser Pro His Tyr Val Glu Phe Pro
         35                  40                  45
Ile Lys Pro Gly Thr Thr Leu Thr Lys Leu Lys Ile Glu Tyr Tyr Val
     50                  55                  60
Glu Trp Ala Leu Asp Ala Thr Ala Tyr Lys Glu Phe Arg Val Val Glu
 65                  70                  75                  80
Leu Asp Pro Ser Ala Lys Ile Glu Val Thr Tyr Tyr Asp Lys Asn Lys
                 85                  90                  95
Lys Lys Glu Glu Ser Phe Pro Ile Thr Glu Lys Gly Phe Val Val Pro
            100                 105                 110
Asp Leu Ser Glu His Ile Lys Asn Pro Gly Phe Asn Leu Ile Thr Lys
        115                 120                 125
Val Ile Ile Glu Lys Lys Gly Ser Ile Glu Gly Arg Ile Thr Tyr Thr
    130                 135                 140
Asp Cys Thr Glu Ser Gly Gln Asp Leu Cys Leu Cys Glu Gly Ser Asn
145                 150                 155                 160
Val Cys Gly Lys Gly Asn Lys Cys Ile Leu Gly Ser Asn Gly Glu Glu
                165                 170                 175
Asn Gln Cys Val Thr Gly Glu Gly Thr Pro Lys Gln Gln Ser His Asn
            180                 185                 190
Asp Gly Asp Phe Glu Glu Ile Pro Glu Glu Tyr Leu Gln
        195                 200                 205
```

```
<210> SEQ ID NO 3
<211> LENGTH: 4
<212> TYPE: PRT
<213> ORGANISM: artificial sequence
<220> FEATURE:
<223> OTHER INFORMATION: synthetic linker peptide

<400> SEQUENCE: 3

Ile Glu Gly Arg
1

<210> SEQ ID NO 4
<211> LENGTH: 4
<212> TYPE: PRT
<213> ORGANISM: artificial sequence
<220> FEATURE:
<223> OTHER INFORMATION: synthetic linker peptide

<400> SEQUENCE: 4

Leu Gly Pro Arg
1

<210> SEQ ID NO 5
<211> LENGTH: 6
<212> TYPE: PRT
<213> ORGANISM: artificial sequence
<220> FEATURE:
<223> OTHER INFORMATION: synthetic linker peptide

<400> SEQUENCE: 5

Gly Ser Ile Glu Gly Arg
1               5

<210> SEQ ID NO 6
<211> LENGTH: 6
<212> TYPE: PRT
<213> ORGANISM: artificial sequence
<220> FEATURE:
<223> OTHER INFORMATION: synthetic linker peptide
```

```
<400> SEQUENCE: 6

Pro Arg Ile Glu Gly Arg
1               5

<210> SEQ ID NO 7
<211> LENGTH: 6
<212> TYPE: PRT
<213> ORGANISM: artificial sequence
<220> FEATURE:
<223> OTHER INFORMATION: synthetic linker peptide

<400> SEQUENCE: 7

Gly Ser Leu Gly Pro Arg
1               5
```